United States Patent [19]
Lebo

[11] Patent Number: 5,654,148
[45] Date of Patent: Aug. 5, 1997

[54] MULTICOLOR IN SITU HYBRIDIZATION METHODS FOR GENETIC TESTING

[75] Inventor: Roger V. Lebo, San Francisco, Calif.

[73] Assignee: The Regents of the University of California, Oakland, Calif.

[21] Appl. No.: 447,655

[22] Filed: May 23, 1995

Related U.S. Application Data

[62] Division of Ser. No. 159,070, Nov. 29, 1993, which is a continuation of Ser. No. 871,967, Apr. 21, 1992, abandoned.

[51] Int. Cl.$^6$ ................................ C12Q 1/68; C12Q 1/70
[52] U.S. Cl. ........................................ 435/6; 435/5
[58] Field of Search ............................ 435/6, 243

[56] References Cited

U.S. PATENT DOCUMENTS 5,427,932  6/1995  Weier et al. ........................ 435/91.2

OTHER PUBLICATIONS

Jacob et al, J. Microsc. 106/2: 185–198 (1976).
Grito et al, Archives of Pathol. & Lab. Medicine 116:395 (5) (1992).
Tobon et al, Archives of Pathol. & Lab. Medicine 115:172(3) (1991).
Weier et al, J. Hischem. Cytochem 38:421–426 (1990).
Encyclopedia Britannica, 15th edition (1994) vol. 2, p. 277
Boehringer Mannheim Catalogue, p. 158.
Burns et al J. Clin. Pathol. 38:1085–1092 (1985).

*Primary Examiner*—Eggerton A. Campbell
*Attorney, Agent, or Firm*—Townsend and Townsend and Crew LLP

[57] ABSTRACT

This invention relates to novel methods of optimally analyzing commonly obtained prenatal cell samples by in situ hybridization. In addition, this method diagnoses gene deletion and gene multiplication using multicolor in situ hybridization. A method is also provided to use multicolor in situ hybridization to identify chromosomal haplotypes co-segregating with disease-related genetic alterations and with normal genes. This haplotype in situ protocol simplifies haplotype segregation analysis in pedigrees.

6 Claims, 2 Drawing Sheets

MULTICOLOR IN SITU HYBRIDIZATION METHODS FOR GENETIC TESTING

This is a division of application Ser. No. 08/159,070 filed Nov. 29, 1993, which is a continuation of application Ser. No. 07/871,967filed Apr. 21, 1992, now abandoned.

This invention was made with Government support under Grant No. NS-25541-01A1, awarded by the National Institute of Health. The Government has certain rights in this invention.

BACKGROUND OF THE INVENTION

1. Field of the Invention

This invention relates generally to multicolor in situ hybridization methods that detect genetic abnormalities. In particular, this invention relates to novel methods to prepare cells for multicolor in situ hybridization and to detect genetic deletions, multiplications, and chromosomal haplotypes associated with genetically related diseases.

2. Brief Description of Background Art

Over 2000 human diseases result from DNA alterations including deletions, multiplications and nucleotide substitutions. Finding genetic disease alterations in individuals and following these alterations in families provides a means to confirm clinical diagnoses and to diagnose disease in carriers, preclinical and subclinical affected individuals, affected unborn fetuses, and preimplantation embryos. Counselling based upon accurate diagnoses allows patients to make informed decisions about potential parenting, ongoing pregnancy, and early intervention in affected individuals.

Disease associated deletions, multiplications, and substitutions may be large or small. Diseases such as steroid sulfatase deficiency, alpha-thalassemia, and Duchenne muscular dystrophy usually result from large deletions. Steroid sulfatase deficiency and alpha-thalassemia patients have common deletion breakpoints while Duchenne muscular dystrophy patients have many deletion and duplication breakpoints. Diseases such as Charcot-Marie-Tooth Disease Type 1A (CMT 1A) have multiple duplication breakpoints that cause the same disease by multiplying the same specific gene(s).

Even in the absence of deletions or multiplications, nucleotide substitutions can result in genetic disease. Multiple alleles within genes are common. Most alleles result from neutral mutations that produce indistinguishable, normally active gene products or express normally variable characteristics like eye color. In contrast, some alleles are associated with clinical disease like sickle cell anemia. Many disease associated alleles co-segregate with specific haplotypes reflected by a unique sequence of neutral nucleotide changes in that gene region. Identifying and following the segregation of affected haplotypes in families provides a means to identify a disease-related gene even when the specific gene mutation is unknown.

Previously diagnosis and confirmation of genetic disease and carrier states often relied upon enzyme activity testing, statistical analysis, or invasive diagnostic procedures. For example, painful nerve conduction tests have been necessary to detect preclinical and subclinical cases of CMT1A, and amniocyte steroid sulfatase assays have been used to prenatally diagnose steroid sulfatase deficiency.

DNA polymorphisms (RFLPs; Restriction fragment length polymorphisms) have been used to diagnose more than 20 genetic diseases reliably (See Lebo et al, Am. J. Hum. Genet. 47:583–590, 1990a, for list). The DNA Committee of the Pacific Southwest Regional Genetics Network proposed that a prenatal clinical test must be informative in at least 70% of fetuses and must be at least 95% reliable (Ibid.). All subsequent communications have agreed with these criteria. The percent informative matings are calculated according to Chakravarti and Buetow, Am. J. Hum. Genet. 37:984–997 (1985), with different formulas for autosomal recessive, autosomal dominant, and X-linked genetic disease. Not all matings are informative because parents may be homozygous for neutral DNA polymorphisms (FIG. 1). The proportion of informative matings depend upon 1) the number of different alleles at each gene locus, 2) the relative frequency of each allele in the population (the most informative have more than one common allele), and 3) whether alleles are distributed randomly throughout the population. Finding enough informative polymorphisms can be very laborious when few or uncommon polymorphisms are found at a disease locus [Lebo et al, Am. J. Hum. Genet. 47:583–590 (1990]. Using characterized polymorphisms may be laborious since several often need to be tested. See, e.g., Lebo et al, Am. J. Med. Genet. 37:187–190, (1990). Even then a proportion of uninformative results in some pedigrees are anticipated. For example, although a substantial number of polymorphic loci have been reported in the CMT1A gene region, multiple polymorphic tests must be used to identify carriers and affecteds. Further complicating accurate diagnosis is the low but real recombination frequency between the reported flanking polymorphisms and the CMT1A locus. Thus for diseases like CMT1A a direct DNA test would provide a more rapid, reliable, and tolerable diagnostic test.

In situ nucleic acid hybridization (in situ hybridization) is the most direct means to map unique chromosome-specific sequences. Originally in situ hybridization used radiolabeled probes to detect target genes [Harper and Saunders, Chromosoma, 83:431–439 (1981)]. While radiolabeled probes detected unique nucleic acid sequences on metaphase chromosomes, detection lacked both speed and resolution. Fluorescent labels conjugated to DNA probes localized targets quickly with high resolution [Langer-Safer et al., Proc. Natl. Acad. Sci. USA, 79:4381–4385 (1982)] to identify single copy genes in metaphase chromosomes [Landegent et al., Nature, 317:175–177 (1985)].

Simultaneously using different colored nucleic acid probes developed for repetitive sequences [Nederlof et al., Cytometry, 10:20–27 (1989)] ordered cosmid clones on a region of uniformly stained chromosome [Lichter et al., Science, 247:64–69 (1990)] and resolved closely spaced DNA clones in interphase nuclei [Trask et al., Genomics, 5:710–717 (1989)]. Different colored probes have been used to demonstrate chromosome translocation in chronic myelogenous leukemia in interphase nuclei [Tikachuk et al., Science, 250:559–562 (1990)].

While substantial nonspecific signal previously limited diagnostic utility, recent studies demonstrated that a 40 kb myophosphorylase cosmid probe gave two unique hybridized signals on every interphase nucleus observed [Lebo et al., Hum. Genet. 86:17–24 (1990)]. This result demonstrated that in situ hybridization to interphase nuclei was sufficiently specific to count gene target number. This specificity has been demonstrated using a Texas red labeled 2 kb keratin cDNA hybridized simultaneously with a yellow-green fluorescein labeled 3 kb flanking genomic sequence that each identify two and only two targets in blue DAPI stained normal interphase nuclei (hereinafter referred to as multicolor in situ hybridization).

Recently protocols have been improved to order 2 kb DNA targets with either Texas red label or yellow-green fluorescein label on blue DAPI banded metaphase chromosomes [Lebo et al., *Hum. Genet.* 88:13–20 (1991); Lebo et al., *Am. J. Hum. Genet.* 50:42–55, 1992]. This improved sensitivity and specificity makes it possible to map small gene probes to morphologically distinguishable chromosome regions. Closely spaced clones within 250 kb have recently been ordered on banded chromosomes. Thus both copies of duplicated disease genes separated by about 250 kb are anticipated to be resolved on early metaphase chromosomes to test for duplicated disease genes directly.

DNA replication that generates a double hybridization signal is difficult to distinguish from true intrachromosomal duplication [Lupsky et al. *Cell,* 68:219–232 (1991)]. Efforts to minimize cells with replicated gene targets have included using confluent amniocyte and fibroblast cultures that have reached stationary phase as well as testing direct amniocytes and chorionic villus cells.

Protocols allowing different cells to be tested by multicolor in situ hybridization would provide extended clinical applicability of this protocol. False negative in situ hybridization results must be minimized by optimally processing and fixing cells to slides according to cell type and slide age. Optimal proteinase K digestion removes histone and nonhistone cellular and chromatin-bound proteins to expose nearly all gene sequences to probe without removing the remaining protein cytoskeleton that holds the nuclear DNA in place. Excessive and under digestion each result in failure to detect gene sequences (false negatives). The same multicolor in situ hybridization protocol that optimally detects lymphocyte genes will detect no genes in cultured fibroblasts. Likewise protocols that work on fresh preparations will detect no sequences on old slides because proteolytic enzyme digestion must be increased to expose unique DNA sequences.

Although in situ hybridization has not been applied to prenatal diagnosis previously, scoring each hybridized cell individually can distinguish common fetal cells from contaminating maternal cells in prenatal samples to give an unambiguous gene deletion or multiplication diagnosis. In contrast, contaminating DNA from nucleated maternal blood cells mixed with direct amniocytes or maternal decidual cells in improperly dissected chorionic villi can be amplified along with fetal DNA by the polymerase chain reaction (PCR) to give false gene signals. Currently restriction enzyme analysis is used to obtain reliable results on DNA extracted from direct amniotic fluid samples from at-risk alpha-thalassemia fetuses so that minor contaminating maternal bands which are significantly lighter do not interfere with diagnosis [Lebo, *Hum. Genet.* 85:293–299, (1990)]. Culturing all tested amniocytes removes maternal blood cells but increases diagnostic time 2–3 weeks. Excellent dissection of chorionic villi will remove nearly all maternal decidual cells, but is technically difficult and requires specialized training. PCR results cannot be trusted with suboptimally dissected chorionic villi because maternal decidual cells grow along with fetal chorionic villus cells. Thus multiple samples may have to be taken when fetal and maternal DNA results do not differ. In contrast, testing cells directly by in situ hybridization can distinguish a small contaminating maternal cell population among the fetal cells because each cell is scored individually. In addition smaller maternal lymphocyte nuclei can be distinguished visually from the larger direct amniocyte nuclei. Thus multicolor in situ hybridization eliminates culture time and false results from maternal cellular DNA amplified indiscriminately by the polymerase chain reaction.

Prior to the present invention, identifying the specific haplotype of a chromosome was cumbersome and time consuming. Chromosomal haplotypes contain many mutations and probing a sufficient number for familial segregation analysis is labor intensive. Despite the many mutations present in a haplotype, the variability between individuals is expected to be small because the races are considered to have diverged about 200,000 years ago based upon no differences in the alpha-globin gene exons in the three races. The intron and gene flanking sequences are expected to have greater variability. Recently HLA intron sequences have been analyzed and homology on the order of 95% has been found. The FCG2 genes which share 98% exon homology have been distinguished from the FCG3 genes which share 98% homologous sequences but differ from the FCG2 genes by about 5% [Lebo et al., *Hum. Genet.* 88:13–20, (1991)]. Prior hybridization protocols were unable to distinguish this level of homology. Haplotype analysis by in situ hybridization is easy and direct even in prenatal samples where maternal contamination can confuse the results.

The present invention overcomes these and other shortcomings by providing a novel combination of multicolor in situ hybridization and analysis of geometric fluorescence patterns to increase the proportion of nuclei correctly scored for genetic aberrations. Methods of multicolor in situ hybridization are provided to allow precise and rapid genetic haplotype analysis. Novel methods of cellular preparation expand the applicability of the claimed methods to prenatal diagnosis.

SUMMARY OF THE INVENTION

Fixation methods for in situ hybridization to amniocytes, chorionic villus cells, fibroblasts, and blastocysts are included for diagnostic and research applications. Using in situ hybridization to uncultured amniocytes and chorionic villus cells provides accurate results quickly from small amniotic fluid volumes or a few villi without expensive, time consuming cell culture.

This novel method also detects abnormal gene number in amniocytes, chorionic villus cells, fibroblasts, and blastocysts. The method comprises obtaining a sample from a patient or fetus, hybridizing a first labeled probe specifically to a chromosomal region adjacent to the gene, simultaneously hybridizing a second labeled probe specifically to said gene, and ascertaining the relative number and positions of the first and second labels in the chromosome complement. Gene deletion is detected in interphase nuclei by scoring interphase nuclei with two flanking gene targets reflecting two intact chromosome regions that have not undergone DNA duplication during cell growth. Then the number of adjacent gene copies are counted. Nuclei with an autosomal gene adjacent to both control spots are normal (FIG. 2C). A nucleus with an autosomal gene adjacent to only one control spot has the second gene deleted (FIG. 2E). Nuclei with two or more genes adjacent to one or both control spots have extra gene copies (FIG. 2D). When scoring metaphase chromosome complements all targets are found on each replicated chromatid and each metaphase chromosome has two chromatids. Thus a single copy gene will have two metaphase chromosome spots on each homologous chromosome and a duplicated gene on that chromosome will have four spots (FIG. 2A, B).

Improved in situ hybridization methods in the present invention identify genetic disease-associated haplotypes. The method comprises obtaining a sample from all appropriate family members including affected patients and at-risk fetuses, hybridizing at least two fluorescently labeled probes specific for different haplotypes of said gene to chromosomes of each sample, wherein each different probe is labeled with a fluorescent label of a different color, observing the color hybridizing specifically to 0, 1, or 2 gene targets per interphase nucleus (0, 2 or 4 targets per metaphase karyotype), and correlating the colors specific for individual haplotypes with segregation of the disease haplotype in the family. As in the most simple application, a flanking probe labeled in one color and a probe specific for the mutation-carrying haplotype in a second color will distinguish 0, 1, or 2 mutant allele haplotypes per cell (FIG. 2F, G).

Kits are also provided to practice the present invention conveniently. These kits contain probes homologous to genes and adjacent DNA regions with different fluorescent labels.

DESCRIPTION OF THE PREFERRED EMBODIMENT

Definitions

Figure 1:
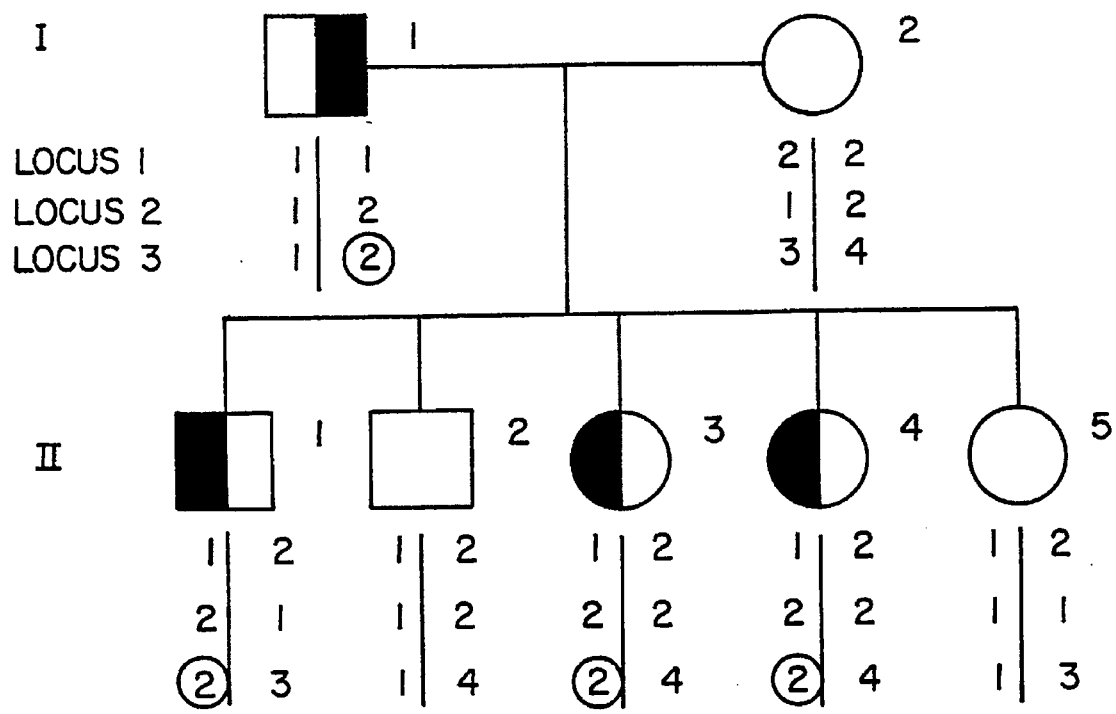
FIG. 1 illustrates segregation of polymorphic markers at three loci at an autosomal dominant genetic disease locus. The polymorphisms in locus 1 are not informative, locus 2 partially informative, and locus 3 fully informative. When a fluorochrome labeled probe specific for locus 3 allele 2 is used, all individuals can be diagnosed correctly by in situ hybridization with 0, 1, or 2 haplotype-specific loci. Additional flanking loci can serve as controls as can different fluorochrome labels for the other alleles.

As used herein, the term "gene" refers to any nucleic acid sequence within a chromosome with a functional role in encoding or transcribing a protein or regulating other gene expression on introns or a flanking genomic sequence which co-segregates with high fidelity. The "gene" may consist of all of the functional nucleic acids responsible for encoding a protein or only a portion of the nucleic acids responsible for encoding or expressing a protein. The nucleic acid subsequences may be within exons, introns, initiation, termination, or promoter sequences or other regulatory sequences. The nucleic acid sequence that results in an altered protein product or altered protein concentration may be of any length. When the term "gene" is used with a disease name, e.g. Charcot-Marie-Tooth Type 1A (CMT1A) gene, the gene is the nucleic acid sequence within the chromosome complement which is multiplied, deleted or otherwise mutated to result in the disease phenotype.

As used herein, the term "adjacent" refers to a flanking gene region on the same chromosome. The adjacent region may be either 3' or 5' to the gene. Although this distance may vary, the flanking sequence must be sufficiently distant so as not to be deleted, multiplied or mutated along with the respective gene in carriers or affecteds. The distance must also be sufficiently small so that fragmentation of interphase nuclei during slide preparation and hybridization will not disrupt hybridization of probes directed to both the gene and the adjacent region in a statistically significant fashion. Fragmentation of metaphase chromosome complements must be sufficiently rare to permit scoring flanking and gene fluorescence of intact banded chromosome complements. In a disease such as CMT 1A in which a gene is multiplied different distances in both directions, the adjacent region will be sufficiently distant in either direction so that it is not multiplied with the gene. Typically minimal distance to "adjacent" sequences refers to a range just distal to the common deletion breakpoint for diseases like alpha-thalassemia to sequences megabases from highly variable, large duplicated chromosome regions as in CMT1A. When two different colored adjacent fluorescent probes are visualized in the same location, the composite color is scored (i.e. red+green=yellow).

As used herein, the term "sample" refers to a collection of biological material from an organism containing nucleated cells. This biological material may be solid tissue as from a fresh or preserved organ or tissue sample or biopsy; blood or any blood constituents; bodily fluids such as amniotic fluid, peritoneal fluid, or interstitial fluid; cells from any time in gestation including prefertilizied or fertilized embryo or preimplantation blastocysts, or any other sample with intact interphase nuclei or metaphase cells no matter how many chromosomes are present. The "sample" may contain compounds which are not naturally intermixed with the biological material such as preservatives anticoagulants, buffers, fixatives, nutrients, antibiotics, or the like.

The biological material must contain substantially intact chromosome complements. As used herein, the term "chromosome" refers to substantially intact chromosomes and the term "chromosome complement" refers to a substantially complete, intact chromosome set. A fragmented chromosome is considered substantially intact provided that the deleted or multiplied gene and the adjacent regions of the chromosome are intact and a sufficient amount of the chromosome is linked to the intact deleted or multiplied gene and adjacent regions to allow identification of the specific chromosome region copy number (e.g. the X chromosome or Y chromosome in the steroid sulfatase gene (STS) assay). A chromosome complement is substantially intact provided that all unknown chromosome regions of interest are intact, accessible, and hybridize to all probes to give the correct number of control flanking chromosome spots and unknown gene copies in the statistically expected frequency. Visualizing multiple gene copies on any chromosome may only occur in a statistically significant fraction of interphase nuclei (i.e. 15–60% for CMT1A) because the duplicated genes are quite close. Chromosome identification may be by means of evenly stained chromosomal DNA in metaphase spreads, traditional metaphase or prometaphase chromosome banding, hybridization to control chromosomespecific sequences with a spectrally unique labeled probe, or other means.

As used herein, the term "predetermined pattern" refers to a previously identified geometrical relationship between probe target position and number on a normal chromosome complement and modified patterns on abnormal chromosome complements. When appropriate, a "predetermined pattern" includes not only the spatial relationship and quantity of different probe targets on interphase nuclei but also on metaphase chromosome complements that are stained uniformly or banded by any chromosome banding procedure. Generally, single adjacent probe targets on normal chromosomes carrying each normal gene type of interest will reflect the "predetermined normal pattern" in the method of the present invention.

As used herein, the term "deletion" refers to the absence of a "gene" in a chromosome complement which results in a specific genetically related disease and perhaps in additional genetic diseases resulting from adjacent gene deletions. At least one additional "gene" is present in chromosome complements of subjects who do not exhibit the disease.

As used herein, the terms "multiplication" or "duplication" refer to the presence of one or more extra "gene" copies in an affected subject's chromosome complement resulting in a specific genetic disease compared to the normal number of "genes" in chromosome complements of subjects without the disease.

As used herein, the term "haplotype" refers to an ordered combination of alleles and/or neutral mutations in a defined chromosome region or chromosome complement. These sequences may be within a gene, between genes, or in an adjacent gene(s) or chromosome region that cosegregates with high fidelity.

As used herein, the term "allele" refers to one of several alternative forms of a "gene" occupying a given chromosome locus.

Fixation methods specifically for in situ hybridization are provided for amniocytes, chorionic villus cells, fibroblasts, and blastocysts. For instance, fibroblasts are preferably prepared in a 75 mM KCl hypotonic solution before fixation. Methods for preparing other cell types are described in detail below. These methods can be used routinely for diagnostic and research samples. Amniocytes from small volumes of direct amniotic fluid and nuclei from a few chorionic villi provide accurate prenatal results without expensive, time consuming cell culture.

In addition a novel method is provided for multicolor in situ hybridization. The method comprises obtaining a sample containing the unknown chromosome complement, using a first labeled probe that hybridizes specifically to a chromosomal region adjacent to the gene, using a second labeled probe which hybridizes specifically to said gene on the chromosome, and ascertaining the relative positions of the first and second labels in the chromosome complement. These relative locations have a predetermined normal geometric pattern in the chromosome complement. Deletion of an autosomal gene in amniocytes, chorionic villus cells, fibroblasts, or blastocysts is detected by identifying more first labeled flanking control DNA targets than the number of second labeled probe gene targets. Multiplication of an autosomal gene is detected by identifying fewer first control labeled probe targets than the number of second labeled probe targets. Additional probes and colors may be added to refine and extend this general procedure to include more loci per haplotype, more tested gene loci or flanking loci per hybridization procedure or sex chromosome testing.

The present invention also provides a novel method for identifying a gene haplotype by multicolor in situ hybridization. This method comprises obtaining a sample with intact patient cell nuclei, hybridizing a first labeled probe specifically to a chromosomal region adjacent to the gene, hybridizing a second labeled probe specifically to a unique haplotype of said gene, and ascertaining the relative position and number of the first and second labels on the chromosome complement. This improved in situ hybridization method provides a means to identify haplotypes associated with genetic diseases. This method comprises obtaining a patient sample including nucleated cells, hybridizing these to at least two fluorescently labeled probes specific for different haplotypes of said gene wherein each different probe is tagged with a different color fluorescent label, observing the color of each hybridizing locus, and correlating probe color, number, and position to the patient's genetic status.

Kits are also provided to practice the present invention conveniently. These kits contain probes homologous to genes and adjacent DNA regions with different fluorescent labels.

Multicolor fluorescence in situ hybridization involves hybridizing two or more fluorescently labeled nucleic acid probes specifically to nucleic acids in a cytological preparation with total DNA labeled using a different colored stain. Probes are labeled with different fluorescent compounds each with a distinguishable color. When the nucleic acid probes are hybridized to cellular nucleic acid sequences, hybridization sites are detected by a unique colored fluorescence emission. Probe signal spacing and order determines the relative chromosomal position and number of homologous nucleic acid sequences.

Chosen probes may hybridize to homologous cellular nucleic acid sequences that are not located in the chromosomal region of interest or are not perfectly homologous to the probes. Also, if the homologous nucleic acid sequence in the cell is not exposed, the probe may not be able to hybridize.

The present invention provides specific methods to use multicolor fluorescence in situ hybridization to detect gene multiplication and deletion in chromosome complements. Target probes which hybridize to nucleic acid sequences within the multiplied or deleted gene segments are used to detect the presence or absence of a gene and its copy number. Location probes which hybridize to nucleic acid sequences flanking the multiplied or deleted gone sequences are used to mark the proper chromosomal region. Detecting a location probe adjacent to the gene provides a means to exclude nonspecific fluorescence signals outside the gene region. Since location probes are adjacent to genes, intact chromosomes with deleted genes will exhibit a location probe without an adjacent target probe while fragmented or missing chromosome regions will not hybridize to either target or location probe and will exhibit no fluorescence.

The in situ hybridization method in the present invention also provides a rapid, reliable, and highly informative means to identify chromosomal haplotypes associated with diseases. Many diseases associated with small mutations (e.g. one nucleotide substitution in sickle cell anemia) cosegregate with a specific chromosomal haplotype. Although the disease-related mutation may be too small to be identified by in situ hybridization, a chromosomal region defining a haplotype can be detected because it is much larger. Identifying a haplotype co-segregating with a disease-related mutation can delineate disease status. Prior methods of in situ hybridization could not distinguish between haplotypes because most haplotypes vary only by about 5%. The present method allows small haplotype differences to be distinguished.

Probes to different haplotypes are used simultaneously. Each probe is labeled with a compound having a different fluorescent color. If a chromosomal region has more haplotypes than can be distinguished by available labels, the different probes can be hybridized to the cells in groups and the different labels bound to only one probe in each group. Following hybridization, the cells are scored. Correlation of labels to probes identifies the chromosomal haplotype. Cells are only scored when a labeled probe flanking the haplotype region hybridizes to both chromosomes in the chromosome complement. This flanking probe signal identifies haplotype chromosome regions that are sufficiently intact and available for hybridization.

Probes are chosen to be within common deleted or duplicated gene regions including exons, introns, and unique adjacent regions. Probes may be either RNA or DNA oligonucleotides or polynucleotides and may contain not only naturally occurring nucleotides but their analogs like digoxygenin dCTP, biotin dCTP, 7-azaguanosine, azidothymidine, inosine, or uridine. The advantages of analogs include greater stability, resistance to nuclease activity, ease of signal attachment, increased protection from extraneous contamination and an increased number of probe-specific colors.

Probes have sufficient complementarity to their target polynucleotides so that stable and specific binding occurs between the chromosome and the probe. The degree of homology required for stable hybridization varies with the stringency of the hybridization medium and/or wash medium. Preferably completely homologous probes are employed in the present invention, but persons of skill in the art will readily appreciate that probes exhibiting lesser but sufficient homology can be used in the present invention.

Probes may be generated and chosen by several means including mapping by in situ hybridization [Landegent et al, *Nature* 317:175-177, 1985], somatic cell hybrid panels [Ruddle & Creagan, *Ann. Rev. Genet.* 9:431, 1981], or spot blots of sorted chromosomes [Lebo et al, *Science* 225:57-59, 1984]; chromosomal linkage analysis [Ott, *Analysis of Human Genetic Linkage*, Johns Hopkins Univ Press, pp.1-197,1985]; or cloned and isolated from sorted chromosome libraries from human cell lines or somatic cell hybrids with human chromosomes [Deaven et al, *Cold Spring Harbor Symp.* LI:159-168, 1986; Lebo et al. *Cold Spring Harbor Symp.* LI:169-176], radiation somatic cell hybrids [Cox et al, *Am. J. Hum. Genet.* 43:A141, 1988], microdissection of a chromosome region [Claussen et al, *Cytometry* 11:suppl 4 p. 12, 1990], (all of which are incorporated by reference), or from yeast artificial chromosomes (YACs) identified by PCR primers specific for a unique chromosome locus (sequence tagged site or STS) or other suitable means like an adjacent YAC clone. Probes may be genomic DNA, cDNA, or viral DNA cloned in a plasmid, phage, cosmid, YAC, or any other suitable vector. A majority of cosmid length probes are excellent because the signal is sufficiently intense and the domain is sufficiently small to identify easily scored domains on interphase nuclei or metaphase chromosomes. Probes may be cloned or synthesized chemically. When cloned, the isolated probe nucleic acid fragments are typically inserted into a replication vector, such as lambda phage, pBR322, M13, pJB8, c2RB, pcos1EMBL, or vectors containing the SP6 or T7 promoter and cloned as a library in a bacterial host. General probe cloning procedures are described in Arrand J. E., *Nucleic Acid Hybridization A Practical Approach*, Hames B. D., Higgins, S. J., Eds., IRL Press 1985, pp. 17-45 and Sambrook, J., Fritsch, E. F., Maniatis, T., *Molecular Cloning A Laboratory Manual*, Cold Spring Harbor Press, 1989, pp. 2.1-3.58, both of which are incorporated herein by reference.

Briefly, the DNA sequences to be cloned are partially or completely digested by cloning-site specific restriction enzyme digestion of selected nucleic acids. The ends of the DNA sequences to be cloned may be modified to minimize ligation to other DNA fragments but still permit ligation to the vector. Other modifications may be made prior to ligation to the vector like blunt ending or addition of homopolymer tails or oligonucleotide linkers. Vector nucleic acids must be cleaved with appropriate restriction enzymes to specifically open the cloning site. The resulting DNA fragments are recovered and tested for ligating efficiency. Acceptable DNA fragments to be cloned are ligated to the acceptable vector. The resulting ligated DNA sequences may then be processed appropriately for the chosen vector. Generally, ligated plasmids are transformed into bacteria, or packaged into a bacteriophage and transfected into bacteria, or introduced into yeast. The bacteria are plated and screened for clones carrying the sequences of interest or pools of yeast clones are grown and the DNA extracted. Additional screening steps including PCR amplification for an STS are used to identify a pool of yeast clones with the DNA sequence of interest. Then clones are plated in an array, grown, and screened with sequence-specific probe. Selected clones are grown and probes extracted by cell lysis and nucleic acid extraction followed by gel electrophoresis, high pressure liquid chromatography, or low or high speed column or gradient centrifugation. Pulsed field gel electrophoresis may be preferred to isolate a pure YAC clone.

Alternatively, oligonucleotide probes may be synthesized chemically with or without fluorochromes, chemically active groups on nucleotides, or labeling enzymes using commercially available methods and devices like the Model 380B DNA synthesizer from Applied Biosystems, Foster City, Calif., using reagents supplied by the same company. Other methods may also be used to synthesize oligonucleotide probes, e.g., the solid phase phosphoramidite method that produces probes of about 15-250 bases. Methods are detailed in Caruthers et al., *Cold Spring Harbor Symp. Quant. Biol.*, 47:411-418, 1982, and Adams, et al., *J. Am. Chem. Soc.*, 105:661, 1983, both of which are incorporated hereinby reference.

Polymerase chain reaction can also be used to obtain large quantities of isolated probes. The method is outlined in U.S. Pat. No. 4,683,202, incorporated herein by reference.

When synthesizing a probe for a specific target, the choice of nucleic acid sequence will determine target specificity. For example, probes may be selected by using commercially available computer programs to compare known DNA sequences from genes sequences found in libraries like Genebank and EMBL. The programs identify unique nucleotide sequences within the gene of interest. One such program is Eugene. Oligonucleotide sequences for PCR of a unique chromosome region can be chosen optimally by choosing sequences according to previously established protocols or by computer programs that choose the degree of homology desired along with the length of the probe. Sequences are chosen to avoid technical problems like primer dimers resulting from amplification of hybridized primers.

Probes may be labeled with several fluorophors or enzymes that generate colored products. The probes used in the assay must be labeled with more than one distinguishable fluorescent or pigment color. These color differences provide a means to identify the hybridization positions of specific probes. Probes may be labeled with Texas red, rhodamine and its derivatives, fluorescein and its derivatives, dansyl, umbelliferone and the like or with horse radish peroxidase, alkaline phosphatase, or the like. Probes that are not separated spatially can be identified by a different color light or pigment resulting from mixing two other colors (light red+green=yellow) pigment (blue+yellow=green) or by using well chosen filter sets that pass only one color at a time.

Probes can be labeled directly or indirectly. The common indirect labeling schemes covalently bind a ligand to the nucleotide and prepare labeled probe by incorporating this using random priming or nick translation. The ligand then binds an anti-ligand which is covalently bound to a fluorescent label. Ligands and anti-ligands vary widely. When a ligand has an anti-ligand, e.g., biotin, thyroxine, or cortisol, the ligand may be used in conjunction with the labelled naturally-occurring anti-ligand. Alternatively, a hapten or antigen may be used in combination with an antibody.

One preferred indirect DNA probe label is bio-11-dUTP (ENZO Diagnostics, New York, N.Y.). First the probes are purified by cesium chloride gradient ultracentrifugation and glass bead extraction with a Gene Clean kit (Bio 101, La Jolla, Calif.). Clean probe (1 microgram) is then mixed with bio-11-dUTP or other DNA probe label along with $^3$HdGTP tracer in the presence of 2 ng DNase per 50 microliter reaction mixture. After nick translation or random priming in the presence of polymerase, nuclease, and unlabeled nucleotides, labeled probe is separated from unincorporated nucleotides with G-50 Sephadex spin columns equilibrated in 150 mM NaCl, 15 mM sodium citrate, 0.1% sodium dodecyl sulfate (pH 7.0). Labeled probes are precipitated with a 50-fold excess of salmon sperm carrier DNA and yeast tRNA. Probes having repetitive sequences are further mixed with 100- to 500-fold excess depurinated human placental DNA. The probes are ethanol precipitated, washed twice in 70% ethanol at 0° C., and dried for 10 minutes at 23° C. in a Savant speed vac. The pellets are redissolved to 8 ng/microliter in 100% deionized formamide for 30 minutes at 37° C. The solution is mixed with an equal volume of 2× SSC, 20% dextran sulfate, 100 mM NAPO4 and denatured for 5 minutes at 90° C. Denatured unique probes are chilled on ice. Probes with repetitive sequences are prehybridized to placental human DNA for 4 hours at 37° C. Fluorescent labels are bound to the probes following hybridization. The same protocol may be followed to incorporate the hapten digoxygenin-11-dUTP (Boehringer, Mannheim, Germany) into probe.

Preferably chromosomal DNA is stained with a spectrally distinguishable DNA specific stain such as DAPI. The chromosome staining provides a background to facilitate the identification of chromosomes and aid in distinguishing the colors and positions of the labels. Typically the chromosome is stained for three minutes with DAPI (Sigma) in McIlv-ane's buffer. The slide is rinsed twice in McIlvane's buffer for two minutes and drained well. Other DNA-specific stains like propidium iodide that uniformly stain chromosomes may be used with at least two other spectrally distinguishable stains or at lower concentrations so as not to obscure one stain color.

The method of the present invention may be practiced on many cell types. Prenatal genetic diagnosis is dependent upon collection of cells of fetal origin. The present invention is particularly useful for prenatal diagnosis of genetic diseases in amniocytes, chorionic villus cells and blastocysts, as well as direct lymphocytes from any fetus or other subject or purified fetal cells from maternal circulation. The safest and most convenient methods of fetal cell collection are amniocentesis and chorionic villus sampling. Because amniocentesis taps fluid which is external to the fetus, the most abundant fetal cells in amniotic fluid are amniocytes. Smaller volumes of relatively pure amniotic fluid samples provide more amniocytes than cells such as lymphocytes which are commonly employed in other genetic analyses. Since viable amniocytes occur in small numbers in the amniotic fluid, larger fluid volumes are needed to provide a sufficient number of cells for restriction enzyme analysis but small volumes are diagnostic by direct multicolor in situ hybridization. Because culture is not required prior to assay with smaller fluid samples, this method is faster and safer. Chorionic villus sampling followed by careful, expert dissection from the maternal decidua provides many high quality cells which are ideal for in situ hybridization to interphase nuclei. Even though culturing is necessary for multiple karyotype analysis, direct in situ hybridization to chorionic villus cells provides an earlier answer than direct in situ hybridization to amniocytes for gene deletions, multiplications, or haplotype analysis. In fact, 95% of the significant chromosome abnormalities in newborns can be detected within 48 hours by in situ hybridization for aneuploidy in 5 chromosomes [Lebo et al., Am. J- Med. Genet. 37:187–190 (1990)].

Following collection, cells must be prepared for hybridization. Different cell types must be prepared differently. Lymphocyte and solid tissue preparation is described in Pardue, M. L., Nucleic Acid Hybridisation, A Practical Approach, Hames, B. D., Higgins, S. J., Eds., IRL Press, 1985, PP. 188–190, incorporated herein by reference. Briefly, lymphocytes are prepared from an aminopterinsynchronized culture. Colcemid is incubated with the culture and removed. Cells are collected by centrifugation and resuspended in hypotonic solution (1:1::0.4% NaCitrate:.4%KCl) for 15 min. After a repeated centrifugation the pellet is resuspended in about 1 ml supernatant and the suspension fixed slowly in Carnoy's fixative (3:1::methanol:glacial acetic acid) for 15 min. After repeated fixation for at least 30 min the cell suspension is dropped on wet, ethanol cleaned slides for hybridization.

Solid tissue is dissected into small pieces and fixed in Carnoy's fix (3:1::methanol:glacial acetic acid). Tissue in the fixative is added to acetic acid on a coverslip. The tissue is minced on the coverslip to release cells. A slide is placed on the coverslip and pressed to squash the cells. The slide is frozen on dry ice and the coverslip is removed. The slide is washed in ethanol and dried for hybridization.

Standard protocols to prepare solid tissue for in situ hybridization are not effective for amniocytes, blastocysts, or chorionic villus cells (either direct or cultured). Generally preparation of these cells includes collection of the cells in amniotic fluid (direct amniocytes), mincing direct chorionic villi and dissociating with 85 U/ml pronase, or detachment from a culture plate by pronase or trypsin digestion (cultured cells). The fluid containing the cells is placed in a 15 ml polypropylene tube. The tube is centrifuged at 200 g for 7 minutes, the supernatant is removed and the cell pellet is gently resuspended by tapping. A hypotonic solution is added dropwise to a total volume of 1–2 ml while gently mixing. The hypotonic solution varies with the cell type. For direct amniocytes and direct chorionic villus cells the hypotonic solution is 1:1::0.2% KCl:0.2% NaCitrate. For cultured amniocytes the hypotonic solution is 1:1::0.4% sodium citrate:0.4% KCl. For cultured chorionic villus cells the hypotonic solution is 1:3::Hanks PBS:$H_2O$.

The solution is incubated in a 37° C. waterbath for 8 minutes and then immediately centrifuged at 200 g for 7 minutes. The supernatant is removed and the cell pellet is dissociated and fixed in 1–2 ml fix (3:1::methanol: glacial acetic acid) added dropwise with gentle tapping. After 15 minutes the solution is centrifuged at 200 g for 7 minutes. The supernatant is removed and the cell pellet dissociated and fixed in 1–2 ml fix added dropwise with gentle tapping. Precleaned cells stored in 100% methanol are chilled in an ice slurry and fixed cells are added dropwise to the slides. Slides are then air dried and examined by phase contrast microscopy to assure an adequate number of attached cells. If an unusually high level of cytoplasm is noted, additional slides can be made and plunged into glacial acetic acid 5 to 60 seconds to remove excess cytoplasm. Suitable slides are baked for 2 hours at 60° C. on a slide warmer.

Blastocysts are derived from preimplantation embryos. A preferred method of cellular preparation and fixation is as follows.

Embryo manipulation is best done under a dissecting microscope at 50× magnification. Embryos may be grown in Ham F10 medium using maternal serum in tissue culture dishes. The embryo is transferred into Ham F10 medium without serum. Then the embryo is transferred into Ham F10 with 1% BSA titrated to pH 2–2.15. After all of visible zona pellucida is dissolved, the embryo is transferred into phosphate buffered saline without calcium or magnesium (Hanks). Then the embryo is transferred into 1% sodium citrate hypotonic solution, transferred to the slide to be tested and fixed to the slide by adding dropwise Carnoy fix (3:1::methanol:glacial acetic acid). The position of the embryo is marked on the bottom of the slide. Dropwise fixation continues until the embryo disappears. Then the slide is fixed overnight in Carnoy's fixative. Subsequent preparation and in situ hybridization is completed according to cultured amniocyte protocols except that fixed cells are treated with approximately 6-fold more proteinase K to remove extra protein. Proteinase K treatment varies according to the number of blastocysts treated, how much zona pellucida remains, the size of the blastocysts which is usually dependent upon the number of divisions completed in the embryo, and the health of the cells tested.

Just prior to hybridization the slides are rehydrated in phosphate buffered saline and treated with proteinase K (100 pg\ml; 100 microliters/slide [Stock solution: 10 mg/ml aged at 37° C. for 3 hours and frozen in aliquots] for 8 minutes at 37° C., then washed for 5 minutes at 23° C. in PBS plus 50 mM $MgCl_2$. The slides are then fixed for 10 minutes at 23° C. in 1% formaldehyde in PBS plus 50 mM $MgCl_2$. The slides are washed twice for 3 minutes at 23° C. in PBS, dehydrated in an ethanol series, then air dried. When dry the slide bound DNA is denatured for 5 minutes at 70° C. in 2× SSC, 70% formamide, 50 mM NaPO4 (pH 7.0). The slides are then chilled in 70% ethanol at 0° C., dehydrated in ethanol, and air dried.

In situ hybridization is carried out on cells fixed to slides. In situ hybridization may be performed by several protocols such as those described in Pardue, M. L., *Nucleic Acid Hybridisation, A Practical Approach*, Hames, B. D., Higgins, S. J., Eds., IRL Press, 1985, pp. 190–198, and John, et al., *Nature*, 223:582–587 (1969), both of which are incorporated hereinby reference.

Various degrees of hybridization stringency can be employed. As the hybridization Conditions become more stringent, a greater degree of complementarity is required between the probe and target to form and maintain a stable duplex. Stringency is increased by raising temperature, lowering salt concentration, or raising formamide concentration. Adding dextran sulfate or raising its concentration can increase the effective concentration of labeled probe to increase the rate of hybridization and ultimate signal intensity. In addition, ultrasonic treatment of the reaction vessel in a commercially available sonication bath may accelerate hybridization.

After hybridization, slides are washed in a solution typically containing reagents similar to those found in the hybridization solution. Ideally the hybridization and initial washing solutions have similar stringencies. The washing time may vary from minutes to hours but longer washes typically lower nonspecific background in proportion to the length of total washing time in all solutions.

A preferred technique follows: Slides are prepared as above and then aged by warming at 60° C. for 2 hours. Aged slides are treated with essentially protease free RNase (Sigma, Cat. No. R5503; 6.5 Kurnitz units/ml) for 60 min in 2× SSC at 37° C. The slides are washed three times 5 min each at 23° C. in 2× SSC, dehydrated in a graded ethanol series, and air dried. The slides were rehydrated 5 min in phosphate-buffered saline [PBS: 100 mM $NAPO_4$; 185 mM NaCl; (pH7.2)], then digested with proteinass K [Boshringer, Mannheim, Germany, Cat. No. 745723; Stock: 200U/ml incubated at 37° C. for 3 hr and stored in frozen aliquots at −20° C. and diluted 1/100,000 in PBS]. After 8 minutes proteinass K digestion at 37° C., slides were washed 5 min in PBS and then the proteinass K was inactivated in 1% formaldehyde in PBS plus 50 mM $MgCl_2$. The slide was washed twice for 3 min in PBS, dehydrated in an ethanol series, and air dried. Chromosomal DNA bound to the slide was denatured 5 min at 70° C. in 2× SSC, 70% formamide, and 50 mM $NaPO_4$ (pH 7.0), chilled in 70% ethanol at 0° C., further dehydrated in ethanol, and air dried.

Labeled denatured probes (2–4 ng/microliter) were added to coverslips and the slides inverted on the coverslips remain inverted in a slide rack during incubation. The probes and slides were hybridized overnight at 37° C. in a moist dark chamber. Following hybridization, the slides were washed 2×15 min in 50% formamide in 2× SSC at 37° C., and then twice in 2× SSC for 30 min prior to washing at high stringency 3×5 min in 0.1× SSC at 60° C. in a shaking waterbath. The slides were blocked with 200 microliters/slide of 4× SSC and 10% fish skin gelatin (Cat. No. G-7765, Sigma, St. Louis, Mo.) for 30 minutes and drained (blocking step). The slides were then incubated with 100 microliters/slide avidin-Texas red (Vector Labs, Burlingame, Calif.) diluted 1:1000 in 4× SSC plus 2% fish skin gelatin for 30 minutes at 37° C. in a moist dark chamber followed by an additional 30 min incubation at 37° C. with biotinylated goat anti-avidin (Vector) diluted 1:100 as before from 1 mg/ml stock (amplification step). Slides were washed 3×5 min and blocked as before. The slides were then incubated with 100 microliters/slide avidin-Texas red diluted 1:1000 in 4× SSC plus 2% fish skin gelatin (FSG) for 30 minutes at 37° C.

Slides are washed and blocked as before followed by an additional incubation for 30 minutes at 37° C. with biotinylated goat antiavidin (Vector) diluted 1:100 in 4× SSC plus 2% FSG. Slides were washed in 4× SSC and 0.1% Tween 40 three times, blocked with fish skin gelatin and drained. The slides were then incubated with 100 microliters/slide avidin-Texas red diluted 1:1000 in 4× SSC plus 2% fish skin gelatin for 30 minutes at 37° C. The slides were stained with DAPI (Sigma) in McIlvane's buffer, rinsed and drained as suggested by the manufacturer. The slides were mounted in anti-fade.

For probes containing digoxygenin, the signal may be amplified with mouse anti-digoxygenin (Sigma). During hybridization with both biotin-bound probes and digoxygenin bound probes the amplification can occur simultaneously. The slides are washed three times in 4× SSC and 0.1% Tween 40, blocked with fish skin gelatin and drained. Then the digoxygenin signal is fluorescently labeled with 100 microliters/slide rabbit anti-mouse FITC (Sigma). The slides are washed again three times in 4× SSC and 0.1% Tween 40, blocked with fish skin gelatin and drained. The slides are further amplified with goat anti-rabbit FITC (Sigma). The slides are washed again in 4× SSC and 0.1% Tween 40 three times and drained. The slides are stained with DAPI (Sigma) in McIlvane's buffer, rinsed, and drained. The slides are mounted in anti-fade.

The slides are analyzed by standard techniques of fluorescent microscopy such as described in Lebo et al, *Hum. Genet.* 88:13-20, 1991, incorporated herein by reference. Preferably photomicrographs are taken of entire chromosome complements including complete karyotypes and whole interphase nuclei. Briefly, each slide is observed in a microscope equipped with appropriate excitation filters, dichroic, and barrier filters. Filters are chosen based on the excitation and emission spectra of the fluorochromes used. Ektachrome 400 color slide film is exposed different lengths of time depending upon the label, signal intensity, and filter chosen. Typically Texas red signal is photographed 30 times longer than blue DAPI signal. Multiple single color or dual color exposures using the proper filters for the chosen labels are performed with the slides left in place on the microscope stage when the filters are changed.

Figure 2A:
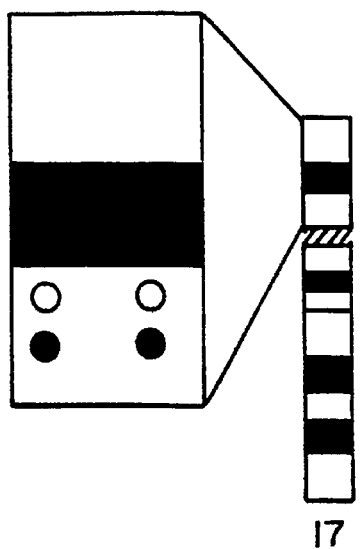
FIG. 2A illustrates a normal chromosome complement with two different fluorescent probes hybridized to a gene (open circles) and an adjacent region (solid circles).
Figure 2B:
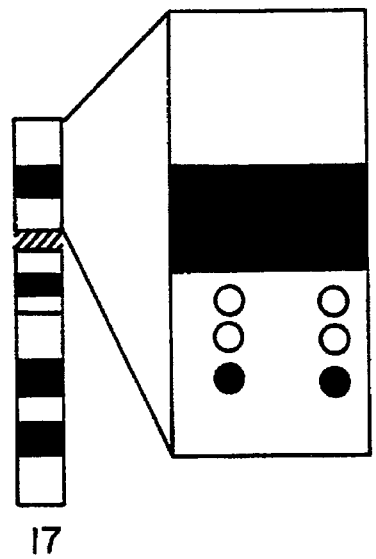
FIG. 2B illustrates a chromosome complement with a duplicated gene with one fluorescent probe hybridized to two genes (open circles) and the other different colored fluorescent probe hybridized to an adjacent region (solid circles). The order is unimportant.
Figure 2C:
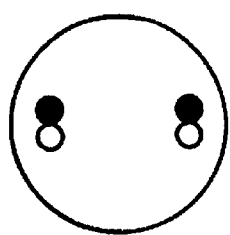
FIG. 2C illustrates a normal interphase nucleus with two different fluorescent probes hybridized to each normal autosomal gene (solid circle) and an adjacent region (open circle).
Figure 2D:
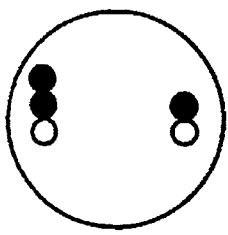
FIG. 2D illustrates the appearance of an interphase nucleus containing the chromosome in 2B with the gene duplicated (left) and the normal chromosome (right).

Gene multiplications are identified by observing a pattern of hybridized probes on a chromosome complement. The probe which is homologous to a region adjacent (adjacent probe) to the multiplied gene provides a marker for the proper gene position. In a normal chromosome the signal for the probe which is homologous to the gene (gene probe) is close to the signal for the adjacent probe. See FIG. 2A and 2C. If the gene is multiplied, there will be more than one signal for the gene probe close to the signal for the adjacent probe. See FIG. 2B and 2D. If the gene is not accessible for hybridization because of chromosome breakage, chromatin-bound proteins, or other factors, neither probe will hybridize. Non-specific binding of the gene probe will be identified by gene probe signal without adjacent probe signal.

Figure 2E:
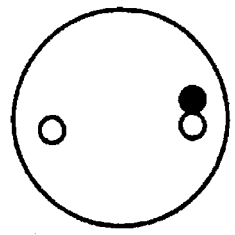
FIG. 2E illustrates an interphase nucleus with an autosomal gene deletion (left) and a normal chromosome (right).

Gene deletions are detected in a similar manner. Signals of the adjacent probe identify chromosome complements able to bind the gene probe when the gene is present. A normal chromosome is identified by an adjacent probe signal lying close to a gene probe signal. See FIG. 2C. If the gene is deleted, the adjacent probe signal is observed alone without a close gene probe signal. See FIG. 2E. If the gene is not accessible for hybridization, neither the adjacent probe nor the gene probe is detected, controlling for false positives.

Figure 2F:
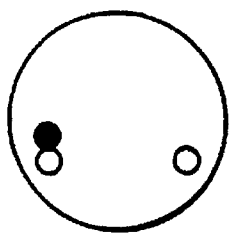
FIG. 2F illustrates an adjacent probe (open circle) hybridized to a chromosome having a haplotype homologous to a haplotype probe (solid circle, left) and a chromosome that does not hybridize to the haplotype-specific probe but does hybridize to the flanking probe (open circle, right).
Figure 2G:
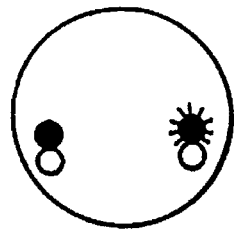
FIG. 2G illustrates an adjacent probe (open circle) hybridized to a chromosome having a haplotype homologous to a haplotype probe (solid circle, left) and a chromosome that does not hybridize to the first haplotype-specific probe but does hybridize to the second haplotype specific probe (dotted circle, right) with a flanking probe (open circle, right).

Chromosome haplotypes are identified by the correlation of detected labels with the respective probes. Preferably an adjacent probe is hybridized to the chromosome to identify the haplotype region. The presence or absence of the adjacent probe provides a control for false negatives and positives as above. Once a hybridized haplotype probe has been detected, the color of the label is correlated with the probe and the haplotype is identified (FIG. 2F and 2G).

EXAMPLES

EXAMPLE I

Preparation of Direct Amniocytes on Slides for In Situ Hybridization:

Five milliliters of amniotic fluid was collected in a 15 ml polypropylene tube. The tube was centrifuged at 200 g for 7 minutes, the supernatant was removed and the cell pellet was gently resuspended by tapping. A hypotonic solution (1:1::0.2% KCl:0.2% NaCitrate) was added dropwise to a total volume of 1-2 ml while gently mixing. The solution was incubated in a 37° C. waterbath for 8 minutes and then immediately centrifuged at 200 g for 7 minutes. The supernatant was removed and the cell pellet was dissociated and fixed in 1-2 ml Carnoy's solution (3:1::methanol: glacial acetic acid) added dropwise with gentle tapping. After 15 minutes the solution was centrifuged at 200 g for 7 minutes. The supernatant was removed and the cell pellet was dissociated and fixed in 1-2 ml Carnoy's solution (3:1::methanol: glacial acetic acid) added dropwise with gentle tapping. Precleaned slides stored in 100% methanol were chilled in an ice slurry and fixed cells were added dropwise to the slides. Slides were then air-dried and examined under a phase contrast microscope to assure an adequate number of cells.

Suitable slides were baked for 2 hours at 60° C. on a slide warmer. Just prior to hybridization the slides were rehydrated in proteinase K buffer (2 mM tris-HCl (pH 7.5) plus 0.2 mM CaCl2), treated with proteinase K (100 pg\ml in proteinase K buffer prepared as before; 100 microliters/slide) for 8 minutes at 37° C., washed for 5 minutes at 23° C. in PBS plus 50 mM $MgCl_2$. The slides were then fixed for 10 minutes at 23° C. in 1% formaldehyde in PBS plus 50 mM $MgCl_2$. The slides were washed twice for 3 minutes at 23° C. in PBS and dehydrated in an ethanol series. The slides were then air dried, denatured for 5 minutes at 70° C. in 2× SSC, 70% formamide, 50 mM NaPO4 (pH 7.0), chilled in 70% ethanol at 0° C., dehydrated in ethanol, and air dried.

EXAMPLE II

Preparation of Direct Chorionic Villus Cells on Slides for In Situ Hybridization.

Chorionic villi were dissected from maternal decidua and minced with a scalpel. Cells in minced tissue were dissociated with pronase (85U/ml) at 37° C. for 20 minutes. The dissociated cells were then centrifuged at 200 g for seven minutes. The supernatant was removed and the cells were prepared according to the protocol of Example I using 1:1::0.2% sodium citrate:0.2% KCl as the hypotonic solution.

EXAMPLE III

Preparation of Cultured Amniocytes on Slides for In Situ Hybridization.

Cultured amniocytes were separated from culture dishes by 0.5 g/L trypsin, 0.2 g/L EDTA, 1.0 g/L glucose, 0.58 g/L $NaHCO_3$ digestion at 23° C. for 1-5 minutes. Trypsin is neutralized and the cells removed with culture medium plus 10% fetal calf serum. Harvested cells were pelleted by centrifugation at 200 g for 7 minutes. The supernatant was removed and the cells were prepared according to protocol of Example I using 1:1::0.4% sodium citrate:0.4% KCl as the hypotonic solution.

EXAMPLE IV

Preparation of Cultured Chorionic Villus Cells on Slides for in Situ Hybridization.

Cultured chorionic villus cells were harvested from culture dishes by trypsin as in Example III. Harvested cells were pelleted by centrifugation at 200 g for 7 minutes. The supernatant was removed and the cells were prepared according to the protocol of Example I using 1:3::Hanks PBS:$H_2O$ as the hypotonic solution.

EXAMPLE V

Preparation of Preimplantation Blastocysts on slides for in situ hybridization.

All embryo manipulation is under a dissecting microscope at 50× magnification. Embryos are grown in Ham F10 medium using maternal serum in 10 cm tissue culture dishes. The embryo is transferred in a siliconized, flame-pulled pasteur pipette with a cotton plug into a 2 well siliconized slide into Ham F10 medium without serum. Then the embryo is transferred into Ham F10 with 1% BSA titrated to pH 2–2.5 by adding 10 N HCl. After all of visible zona pellucida is dissolved, the embryo is transferred into phosphate buffered without calcium or magnesium (Hanks). Then the embryo is transferred into 1% sodium citrate hypotonic solution for 2 min, transferred to the slide to be tested with teflon-surrounded wells, and fixed to the slide by adding dropwise Carnoy fix (3:1::methanol:glacial acetic acid). The position of the embryo is marked on the bottom of the slide with a diamond tip pencil. Dropwise fixation continues until the embryo disappears. Then the slide is fixed overnight in Carnoy's fixative in a capped 50 ml Corning polypropylene tube. Subsequent preparation and in situ hybridization is completed according to cultured amniocyte protocols except that fixed cells are treated with approximately 6-fold more proteinase K to remove extra protein. Proteinase K treatment varies according to the number of blastocysts treated, how much zona pellucida remains, the size of the blastocysts which is usually dependent upon the number of divisions completed in the embryo, and the health of the cells tested.

EXAMPLE VI

Detection of gene deletion resulting in steroid sulfatase deficiency.

Steroid sulfatase deficiency is an X-linked genetic disorder resulting form deletion of the steroid sulfatase gene on the X chromosome. Multicolor in situ hybridization was performed to identify normal, carrier and disease states.

Cosmid CY437 carries a 40 kb insert homologous to a DNA sequence located about 100 kb 5' to the steroid sulfatase gene on the X chromosome. Only X chromosomes having the steroid sulfatase gene hybridize to cosmid CY437. X chromosomes lacking the steroid sulfatase gene (i.e. from carrier or disease states) do not hybridize to cosmid CY437.

Cosmid CS12 carries a 32 kb Y chromosome derived flanking insert homologous to a nucleic acid sequences on both the X and Y chromosomes. The homologous X chromosome-specific sequence flanking the steroid sulfatase gene is not deleted in X-linked ichthyosis patients when the steroid sulfatase gene has been deleted. Hybridization of CS12 accurately identifies all X and Y chromosomes and facilitates detection of specific cosmid CY437 signal.

Cosmid CY437 was labeled with bio-11-dUTP (ENZO Diagnostics, New York, N.Y.). Cosmid CS12 was labeled with digoxygenin 11-dUTP (Boehringer-Mannheim, Mannheim, Germany). Both probes were labeled by nick translation along with 3H-dGTP tracer with DNAse in a concentration of 2 ng/microliter hybridization mix. Labeled probes were separated from unlabeled DNA with G-50 Sephadex spin columns equilibrated with 150 mM NaCl, 15 mM NaCitrate, and 0.1% SDS (pH 7.0). The labeled probes averaged 200–500 base pairs long and had 30%–60% 3H-dGTP carrier incorporated. Labeled probes with unique and repetitive DNA sequences were precipitated with a fifty-fold excess of salmon sperm carrier DNA and of yeast tRNA, and 100 to 500-fold excess of depurinated human placental DNA (Sigma, St. Louis, Mo.). The precipitated DNA was washed in 70% ethanol and dried in a Savant speed vac. The dried DNA pellets were redissolved to a concentration of 4 ng/ml in 100% deionized formamide and mixed to a final concentration of 1× SSC in 10% dextran sulfate and 50 mM $NaPO_4$ (pH 7.0). The resulting dissolved DNA was denatured at 95° C. in a heat block and prehybridized for 4 hours at 65° C. prior to adding to the slide.

Amniocytes were prepared and fixed to slides as in Example 1 above. Labeled probes were added to the slides at a concentration of 4 ng/microliter and the slides inverted. The probes and samples were hybridized overnight at 37° C. Following overnight hybridization, the slides were washed in 50% formamide in 2× SSC and then in 2× SSC prior to washing at high stringency in 0.1× SSC at 60° C. The slides were blocked with 200 microliters/slide of 4× SSC and 10% fish skin gelatin (Cat. No. G-7765, Sigma, St. Louis, Mo.) for 30 minutes and drained (blocking step). The slides were then incubated with 100 microliters/slide avidin-Texas red diluted 1:1000 in 4× SSC plus 2% fish skin gelatin for 30 minutes at 37° C., washed, blocked, and incubated for 30 minutes at 37° C. with biotinylated goat anti-avidin (Vector) diluted 1:100 in 4× SSC; 2%FSG (amplification step). Slides were washed in 4× SSC and 0.1% Tween 40 three times, blocked with fish skin gelatin and drained (washing step). The blocking step, amplification step, and washing step were repeated.

A Zeiss photomicroscope was used to take photomicrographs with Kodacolor 400 ASA film (Eastman-Kodak, Rochester, N.Y.). DAPI stained interphase nuclei and banded metaphase chromosomes were photographed through a Hoechst filter set [excitation 360 WB50 #9008, dichroic 470 #8902, emission 470 DF65 #8902]. Fluorescein and rhodamine signals were photographed either separately through label specific filter sets or simultaneously through a fluorescein-Texas red filter set or a rhodamine-fluorescein filter set from Omega Optical, Battleboro, Vt. The FITC filter set specifications were excitation 480 DF30 #8902, dichroic 505DRLP #8902, emission 535 DK45 #8902. The Texas red filter set specifications were excitation 560 DF40 #8902, dichroic 595 DRLP #8902, emission 635 DF60 #8902.

Eighty to ninety percent of tested samples revealed two fluorescein-labeled CS12 hybridization spots. Cells exhibiting two green (CS12) spots (indicating hybridization of both sex chromosomes) were scored for the number of red (CY437) spots to detect the steroid sulfatase gene. It was possible to distinguish affected males from normal males, carrier females, and normal females.

All control males and normal males revealed one red (CY437) spot. Three of 43 cells from affected males showed weak red (CY437) spots. When compared to normal males and females the dim character of the red (CY437) spots in the affected males was clearly differentiated. Four of forty four carrier female cells showed two red (CY437) spots. All other female cells showed 1 red (CY437) spots. Two of 20 normal female cells had one red (CY437) spot. The remaining females had 2 red (CY437) spots.

TABLE 1

| SLIDE DESIGNATION | RED: CY437 (X) No. Scored | | | CLINICAL STATUS |
| --- | --- | --- | --- | --- |
| | 0 | 1 | 2 | |
| Control | 0 | 20 | 0 | normal male |
| Unknown #1 | 20 | 2 | 0 | affected male |
| Unknown #2 | 0 | 2 | 20 | normal female |
| Unknown #3 | 20 | 1 | 0 | affected male |
| Unknown #4 | 0 | 20 | 0 | carrier female |
| Unknown #5 | 0 | 20 | 4 | carrier female |
| Unknown #6 | 0 | 20 | 0 | normal male |

EXAMPLE VII

Detection of gene multiplication resulting in Charcot-Marie-Tooth Disease Type 1A.

CMT 1A is a disease associated with duplication of a gene on the short arm of chromosome 17. Multicolor in situ hybridization was performed prenatally to identify carrier and affected individuals. Cells were fixed on slides according to the procedures of Examples I-IV. Cosmid probe 6G1 mapped to the most commonly duplicated CMT1A gene region is the "gene" probe and centromeric probe D17Z1 was the flanking control probe.

Centromeric probe D17Z1 was labeled with bio-11-dUTP (ENZO Diagnostics, New York, N.Y.). Cosmid 6G1 probe was labeled with digoxygenin 11-dUTP (Boehringer-Mannheim, Mannheim, Germany). Both probes were labeled by nick translation along with 3H-dGTP tracer with DNAse in a concentration of 2 ng/50 microliter reaction mix. Labeled probes were separated from unlabeled DNA with G-50 Sephadex spin columns equilibrated with-150 mM NaCl, 15 mM NaCitrate, and 0.1% SDS (pH 7.0). The labeled probes averaged 200–500 base pairs long and had 30%-60% 3H-dGTP content. Labeled probes which contained unique DNA sequences were precipitated with a fifty-fold excess of salmon sperm carrier DNA and yeast tRNA, and to probes like whole cosmids with some unique and some repetitive sequences an additional 100 to 500-fold excess of depurinated human placental DNA (Sigma, St. Louis, Mo.) was added. The precipitated DNA was washed in 70% ethanol and dried in a Savant speed vac. The dried DNA pellets were redissolved to a concentration of 4 ng/microliter in 100% deionized formamide and mixed to a final concentration of 1× SSC in 10% dextran sulfate and 50 mM NaPO4 (pH 7.0). The resulting dissolved DNA was denatured in hybridization mix and probes with unique and repetitive sequences were prehybridized 4 hours at 65° C. to preanneal the repetitive labeled sequences to unlabeled placental DNA repeats. Prehybridization was skipped for moderately repetitive probes like chromosome-specific repetitive sequences.

Preannealed probe in hybridization solution was added to coverslips. Inverted slides were added to the coverslips, placed on slide racks, hybridized overnight at 37° C. Following overnight hybridization, the slides were washed in 50% formamide in 2× SSC and then in 2× SSC prior to washing at high stringency in 0.1× SSC at 60° C. The slides were blocked with 200 microliters/slide of 4× SSC and 10% fish skin gelatin (Cat. No. G-7765, Sigma, St. Louis, Mo.) for 30 minutes and drained (blocking step). The slides were then incubated with 100 microliters/slide avidin-Texas red diluted 1:1000 in 4× SSC plus 2% fish skin gelatin for 30 minutes at 37° C., washed, blocked, and incubated for 30 minutes at 37° C. with biotinylated goat anti-avidin (Vector) diluted 1:100 in 4× SSC; 2%FSG (amplification step). Slides were washed three times in 4× SSC and 0.1% Tween 40, blocked with fish skin gelatin and drained (washing step). The blocking step, amplification step, and washing step were repeated.

A Zeiss photomicroscope was used to take photomicrographs with Kodacolor 400 ASA film (Eastman-Kodak, Rochester, N.Y.). DAPI stained interphase nuclei and banded metaphase chromosomes were photographed through a Hoechst filter set [excitation 360 WB50 #9008, dichroic 470 #8902, emission 470 DF65 #8902]. Fluorescein and rhodamine signals were photographed either separately through label specific filter sets or simultaneously through a fluorescein-Texas red filter set or a rhodamine-fluorescein filter set from Omega Optical, Battleboro, Vt. The FITC filter set specifications were excitation 480 DF30 #8902, dichroic 505DRLP #8902, emission 535 DK45 #8902. The Texas red filter set specifications were excitation 560 DF40 #8902, dichroic 595 DRLP #8902, emission 635 DF60 #8902.

A pregnant woman was shown to have CMT1A gene duplication by RFLP analysis. Fetal cells were tested for CMT1A gene duplication by RLLP analysis. The fetal DNA was uninformative for four RFLP's with three polymorphic DNA probes. Multicolor in situ hybridization clearly demonstrated a duplication of the CMT1A gene only 48 hours after receiving the fetal cells.

EXAMPLE VIII

Prenatal Identification of Chromosomal Haplotypes

Figure 3:
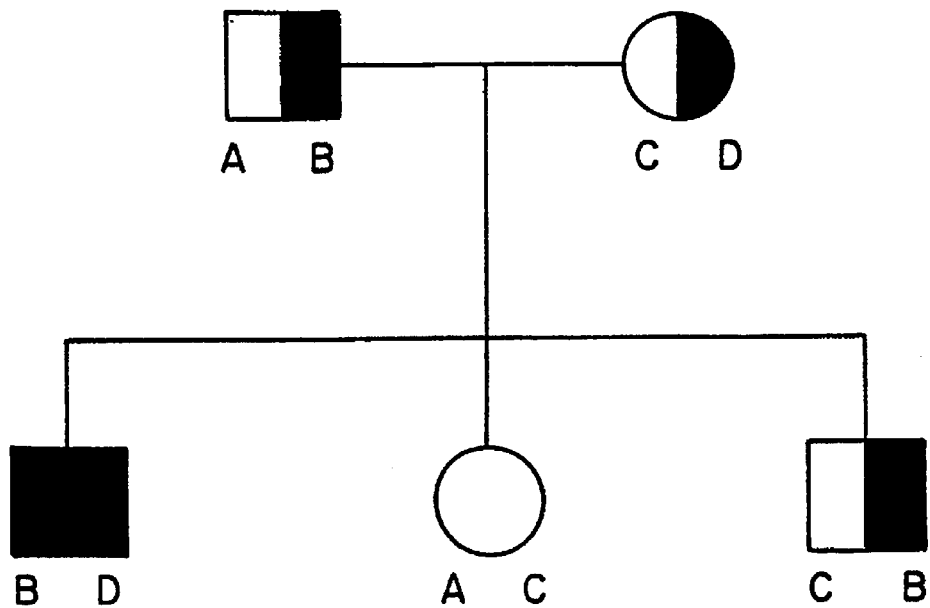
FIG. 3 illustrates the segregation of informative alleles for an autosomal recessive genetic disease. A single fluorochrome identifying both alleles in the affected patient can test carrier status directly in other family members as in FIG. 2F.

Differences of 5% sequence homology between the FCG2 and FCG3 genes can be distinguished by high stringency multicolor in situ hybridization (Lebo et al, 1991). Differences in HLA allele introns differ by 5% (Genetype Corp., International HLA Meeting, Bombay, 1991). These data anticipate that in situ hybridization to the dozen or so specific HLA haplotypes with haplotype-specific probes will distinguish different alleles. Whether introns at other standard gene loci differ by 5% is unknown because selection may require more heterogeneity at the HLA locus. Nevertheless the number of haplotypes at the beta-globin locus is less than the anticipated number of randomly mixed polymorphic haplotypes so that all beta-thalassemia mutations will have arisen on one of these subset of existing haplotypes [Orkin et al., Nature 296:627–631, (1982)]. Nevertheless, flanking gene regions are anticipated to be under less selection pressure so that sequences within 0.3 Mb that combine with an allele less than 1% per meiosis could be tested to follow disease allele segregation in any family. For diseases like Huntington's disease which for which more than 95% probably arose from a single founder gene mutation, a single disease-specific probe will be sufficient to diagnose nearly all at-risk patients. For diseases with a few founder mutations like sickle cell anemia, a few allele-specific probes will distinguish most mutant alleles. Other diseases resulted from multiple severe mutations at the same locus: >120 cystic fibrosis mutations, >80 hemophilia A mutations, one-third of all Duchenne muscular dystrophy mutations are new mutations. For these diseases a limited number of probes against the small subset of founder haplotypes like those found at the HLA and beta-globin loci are expected to distinguish nearly all alleles in all families. Thus in situ hybridization is a unique way to test multiple neutral mutation sites instead of testing one RFLP site at a time with PCR amplification and digestion or restriction enzyme analysis. Which alleles are in each subject can be determined by multiple color labels attached one to each different allele and tested on enough slides to test each haplotype. The more different colored, sensitive, distinguishable fluorochrome schemes become available, the fewer the required slide number to identify affected haplotypes. Segregation of parental haplotypes ware followed by color labeling as demonstrated in FIGS. 1 for autosomal dominant disease, and FIG. 3 for autosomal recessive genetic disease.

What is claimed is:

1. A method of preparing direct amniocytes for in situ hybridization comprising:

collecting a sample of amniocytes;

suspending the direct amniocytes in 1:1::0.2% KCl:0.2% NaCitrate to form a first suspension;

incubating said first suspension, and removing substantially all of said 1:1::0.2% KCl:0.2% NaCitrate; resuspending the amniocytes in Carnoy's solution to form a second suspension;

applying a portion of the second suspension to a glass slide.

2. A method of preparing direct chorionic villus for in situ hybridization comprising:

collecting cells for in situ hybridization and dissecting chorionic villi from maternal descidua;

suspending the chorionic villi in 1:1::0.2% KCl0.2% Nacitrate to form a first suspension;

removing substantially all of the 1:1::0.2 KCl:0.2% NaCitrate;

resuspending said chorionic villi in Carnoy's solution to form a second suspension;

applying a portion of the second suspension to a glass slide.

3. A method of preparing cultured amniocytes for in situ hybridization comprising:

suspending the amniocytes in 1:1::0.4% NaCitrate:0.4 KCl to form a first suspension;

removing substantially all of the 1:1::0.4% NaCitrate:0.4% KCl;

resuspending the amniocytes in Carnoy's solution to form a second suspension;

applying a portion of the second suspension to a glass slide.

4. A method of preparing cultured chorionic villus cells for in situ hybridization comprising:

culturing chorionic villus cells to confluence and harvesting these cultures by pronase digestion;

suspending the chorionic villus cells in 1:3::Hanks $PBS:H_2O$ to form a first suspension removing substantially all of the 1:3::Hanks $PBS:H_2O$;

resuspending the chorionic villus cells in Carnoy's fixative to form second suspension;

applying a portion of the second suspension to a glass slide.

5. A method of preparing fibroblasts for in situ hybridization comprising:

harvesting fibroblasts by standard trypsin digestion, centrifuging the sample to form a first cell pellet and removing the fluid;

resuspending the fibroblasts in a 75 mM KCl hypotonic solution to form a first suspension;

removing substantially all of the 75 m MKCl hypotonic solution;

resuspending the fibroblasts in Carnoy's solution to form second suspension;

applying a portion of the second suspension to a glass slide.

6. A method of preparing blastocysts for in situ hybridization comprising:

placing a blastocyst in 1% sodium citrate solution;

placing the blastocyst on a slide; and placing Carnoy's fixative on the blastocyst.

* * * * *